US012590144B2

(12) United States Patent
Ageeva et al.

(10) Patent No.: US 12,590,144 B2
(45) Date of Patent: Mar. 31, 2026

(54) CARDIAC TROPONIN I SPECIFIC ANTIBODY, KIT AND USES THEREOF

(71) Applicant: SHENZHEN MINDRAY BIO-MEDICAL ELECTRONICS CO., LTD., Shenzhen (CN)

(72) Inventors: Ludmila V. Ageeva, Shenzhen (CN); Anastasia V. Bereznikova, Shenzhen (CN); Agnessa P. Bogomolova, Shenzhen (CN); Alexey G. Katrukha, Shenzhen (CN); Stanislav V. Kozlovsky, Shenzhen (CN); Anfisa S. Popova, Shenzhen (CN); Alexander B. Postnikov, Shenzhen (CN); Fedor N. Rozov, Shenzhen (CN); Natalia N. Tamm, Shenzhen (CN); Yi Zhang, Shenzhen (CN); Sheng Luo, Shenzhen (CN); Puguang Chen, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 6 days.

(21) Appl. No.: 18/479,371

(22) Filed: Oct. 2, 2023

(65) Prior Publication Data

US 2024/0117024 A1 Apr. 11, 2024

(30) Foreign Application Priority Data

Sep. 30, 2022 (CN) .......................... 202211208451.5

(51) Int. Cl.
| | |
|---|---|
| *C07K 16/18* | (2006.01) |
| *A61K 47/68* | (2017.01) |
| *G01N 33/68* | (2006.01) |

(52) U.S. Cl.
CPC .......... *C07K 16/18* (2013.01); *A61K 47/6897* (2017.08); *G01N 33/6887* (2013.01); *C07K 2317/92* (2013.01)

(58) Field of Classification Search
None
See application file for complete search history.

(56) References Cited

U.S. PATENT DOCUMENTS 7,285,418 B2   10/2007   Katrukha et al.

FOREIGN PATENT DOCUMENTS

| CN | 103173420 A | 6/2013 |
|---|---|---|
| CN | 111018974 A | 4/2020 |
| CN | 111018982 A | 4/2020 |
| CN | 111308084 A | 6/2020 |
| CN | 117801100 A | 4/2024 |

OTHER PUBLICATIONS

Cummins et al. "Cardiac-specific troponin-I radioimmunoassay in the diagnosis of acute myocardial infarction", American Heart Journal, Jun. 1987 volume 113, 12 pages.
Bodar et al. "Development of Monoclonal Antibodies for an Assay of Cardiac Troponin-I and Preliminary Results in Suspected Cases of Myocardial Infarction", Clinical Chemistry, vol. 38, No. 11, 1992, 12 pages.
Extended European Search Report issued in related European Application No. 23201248.4, mailed Jan. 31, 2024.
Gregory Lee et al: "Monoclonal antibodies against human cardiac troponin I for immunoassays II" Monoclonal Antibodies in Immunodiagnosis and Immunotherapy, vol. 34, No. 3, Jun. 1, 2015, pp. 169-173, XP055700550, US ISSN: 2167-9436, DOI: 10.1089/mab. 2014. 0088.
Yaghoub Safdari et al: "Antibody humanization methods—a review and update", Biotechnology and Genetic Engineering Reviews, vol. 29, No. 2, Oct. 1, 2013 (Oct. 1, 2013), pp. 175-186, XP055250530, GB ISSN: 0264-8725, DOI: 10.1080/02648725.2013.801235.
First Office Action of the European application No. 23201248.4, issued on Nov. 17, 2025.
Rudikoff S et al.: "Single amino acid substitution altering antigen-binding specificity", Proceedings of the National Academy of Sciences (PNAS), National Academy of Sciences, vol. 79, Mar. 1, 1982 (1982-03-01), pp. 1979-1983, XP007901436, Issn: 0027-8424, Doi: 10.1073/PNAS.79.6.1979, the whole document.
Partial Supplementary European Search Report in the European application No. 25167189.7, mailed on Nov. 14, 2025.
Supplementary European Search Report in the European application No. 25167189.7, mailed on Feb. 4, 2026.

*Primary Examiner* — Maher M Haddad
(74) *Attorney, Agent, or Firm* — Syncoda LLC; Feng Ma

(57) ABSTRACT

The present disclosure provides an antibody specifically targeting cardiac troponin I. The present disclosure further provides antibody pairs and kits comprising the antibodies. The present disclosure further provides the use of these antibodies to detect levels of cardiac troponin I, and to diagnose myocardial injury.

13 Claims, 1 Drawing Sheet

Specification includes a Sequence Listing.

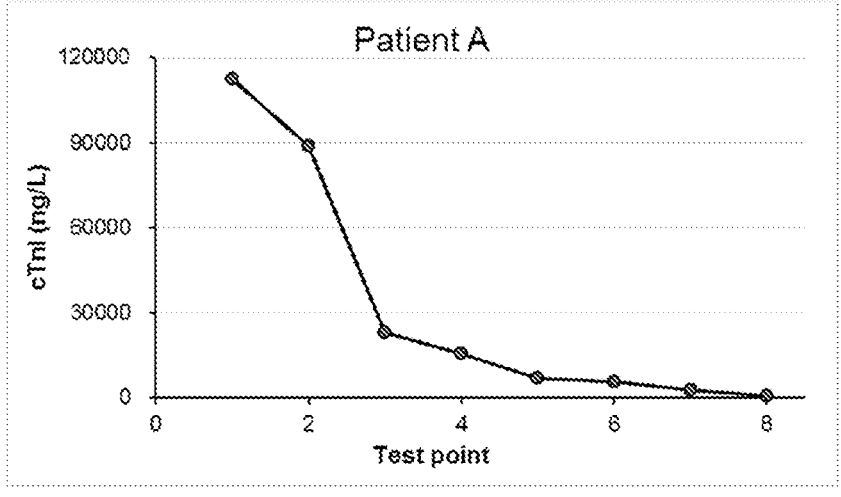

CARDIAC TROPONIN I SPECIFIC ANTIBODY, KIT AND USES THEREOF

CROSS-REFERENCE TO RELATED APPLICATIONS

The application claims the benefit of priority to Chinese Patent Application No. 202211208451.5 filed on Sep. 30, 2022, titled "Cardiac troponin I specific antibody, kit and uses thereof", the entire contents of which are incorporated herein by reference.

REFERENCE TO AN ELECTRONIC SEQUENCE LISTING

The contents of the electronic sequence listing (2313072-I-US-SZMR.xml; Size: 26,868 bytes; and Date of Creation: Nov. 22, 2023) is herein incorporated by reference in its entirety.

TECHNICAL FIELD

The disclosure relates to the technical field of molecular immunology. In particular to an antibody that specifically targets cardiac troponin I, and an antibody pair, kit that comprise the antibody and use thereof.

BACKGROUND

Troponin (Tn) is a regulatory protein of muscle tissue contraction. It is located on the thin filaments of contractile proteins and plays an important role in regulating muscle contraction and relaxation. Troponin contains 3 subtypes: fast-response, slow response type and cardiac troponin (cTn). The first two are related to skeletal muscle, while cardiac troponin exists only in cardiomyocytes and is composed of three subunits: troponin T(cTnT), troponin I(cTnI), and troponin C(cTnC). Cardiac troponin is degraded from myocardial fibers upon myocardial cell injury. Elevated cTn in serum reflects cardiomyocyte damage. Cardiac troponin I is often used to detect myocardial injury, e.g., myocardial infarction, coronary sclerosis syndrome, myocarditis, pericarditis, and the like.

A method for measuring cardiac troponin I in serum is developed by Cummins et al. (Cummins et al., Am Heart Journal 113:1333-1344(1987)). However, polyclonal antibodies with significant cross-reactivity to skeletal forms of troponin I were used in the analysis. In addition, a sandwich analysis is developed by Bodar et al. (Bodar et al., Clinical Chemistry 38:2203-2214(1992); see also U.S. Pat. No. 7,285,418). Unfortunately, such assays have a low accuracy.

Therefore, there is a need to detect cardiac troponin I with high sensitivity and accuracy, and which does not cross-react with troponin I of skeletal muscle. With such an immunological test method, the treating physician can use the appropriate treatment to provide the best possible prognosis for the patients affected by. The present disclosure satisfies these needs.

SUMMARY

In view of this, the present disclosure discloses an antibody or an antigen-binding fragment(s) thereof that specifically targets cardiac troponin I, and related compositions, reagents and methods.

According to a first aspect of the disclosure, the present disclosure provides an isolated antibody or antigen-binding fragment(s) thereof that specifically binds to cardiac troponin I, including a heavy chain and a light chain, wherein the heavy chain includes a heavy chain variable region, and the light chain includes a light chain variable region, where the heavy chain variable region includes:

a. CDR-H1, comprising the sequence of SEQ ID NO.1;
    b. CDR-H2, comprising the sequence of SEQ ID NO.2; and
    c. CDR-H3, comprising the sequence of SEQ ID NO.3; the light chain variable region includes:
    a. CDR-L1, comprising the sequence of SEQ ID NO.4;
    b. CDR-L2, comprising the sequence of SEQ ID NO.5; and
    c. CDR-L3, comprising the sequence of SEQ ID NO.6.

In some specific embodiments, the antibody or antigen-binding fragment(s) thereof, where the heavy chain variable region includes CDR-H1 as shown in SEQ ID NO.1, CDR-H2 as shown in SEQ ID NO.2, and CDR-H3 as shown in SEQ ID NO.3.

In some specific embodiments, the antibody or antigen-binding fragment(s) thereof, where the light chain variable region includes CDR-L1 as shown in SEQ ID NO.4, CDR-L2 as shown in SEQ ID NO.5, and CDR-L3 as shown in SEQ ID NO.6.

In some specific embodiments, the antibody or antigen-binding fragment(s) thereof, where the heavy chain of the antibody or antigen-binding fragment(s) thereof includes the three heavy chain CDRs described above, namely CDR-H1, CDR-H2, and CDR-H3.

In some specific embodiments, the antibody or antigen-binding fragment(s) thereof, where the light chain of the antibody or antigen-binding fragment(s) thereof includes the three above-mentioned light chain CDRs, namely CDR-L1, CDR-L2, and CDR-L3.

In some specific embodiments, the antibody or antigen-binding fragment(s) thereof, which includes CDR-H1 as shown in SEQ ID NO.1, CDR-H2 as shown in SEQ ID NO.2, and CDR-H3 as shown in SEQ ID NO.3; and CDR-L1 as shown in SEQ ID NO.4, CDR-L2 as shown in SEQ ID NO.5, and CDR-L3 as shown in SEQ ID NO.6.

In some specific embodiments, the antibody or antigen-binding fragment(s) thereof has a KD value of less than 20 nM. For example, KD value is less than 15 nM, 12 nM, 10 nM, 8 nM, 5 nM, 4 nM, 3 nM, 2 nM, 1 nM, 0.5 nM. Preferably, the KD value is measured by biofilm interference technology.

In some specific embodiments, the antibody is a monoclonal antibody.

In some specific embodiments, the antibody or antigen-binding fragment(s) thereof includes non-CDR regions.

In some specific embodiments, the non-CDR regions may or may not be homologous to the CDR regions.

In some specific embodiments, the antibody or antigen-binding fragment(s) thereof, where the antibody or antigen-binding fragment thereof is selected from the group comprising Fab, Fab', F(ab')$_2$, Fd, Fv, dAb, complementarity determining regions fragments, single chain antibodies (e.g., scFvs), humanized antibodies, chimeric antibodies, or diabodies.

In yet another aspect, the present disclosure provides an isolated nucleic acid molecule comprising a nucleotide sequence encoding an antibody or antigen-binding fragment thereof as previously described.

In some specific embodiments, the nucleic acid molecule comprises nucleic acid molecule A, which encodes the heavy chain of the aforementioned antibody or antigen-binding fragment(s) thereof, where the heavy chain includes CDR-H1, CDR-H2, and CDR-H3.

In some specific embodiments, the nucleic acid molecule comprises nucleic acid molecule B, which encodes the light chain of the aforementioned antibody or antigen-binding fragment(s) thereof, where the light chain includes CDR-L1, CDR-L2, and CDR-L3.

In some specific embodiments, the nucleic acid molecule comprises nucleic acid molecule C, the aforementioned nucleic acid molecule A, and the aforementioned nucleic acid molecule B; optionally, the nucleic acid molecule C further includes a linker sequence, which is used to connect the nucleic acid molecule A and the nucleic acid molecule B.

In yet another aspect, the present disclosure provides a vector comprising the aforementioned nucleic acid molecule.

In some specific embodiments, the vector includes nucleic acid molecule A, nucleic acid molecule B, or nucleic acid molecule C as described above.

In another aspect, the present disclosure provides a host cell comprising the aforementioned nucleic acid molecule or the vector.

In some specific embodiments, the host cell comprises the aforementioned nucleic acid molecule A, nucleic acid molecule B, nucleic acid molecule C, or the aforementioned vector.

In yet another aspect, the present disclosure provides a conjugate comprising a monoclonal antibody or an antigen-binding fragment(s) thereof and a coupling moiety, where the monoclonal antibody is the antibody or antigen-binding fragment thereof of the present disclosure, the coupling moiety is a detectable label; preferably, the coupling moiety is a radioisotope, a fluorescent substance, a luminescent substance, a colored substance or an enzyme.

In yet another aspect, the present disclosure provides an antibody pair comprising a capture antibody and a detection antibody, where the capture antibody and the detection antibody target different epitopes of cardiac troponin I, where one of the capture antibody and the detection antibody are selected from an antibody or an antigen-binding fragment thereof as described above, and the others are selected from the group consisting of Known Antibody 1 (KA1), Known Antibody 2 (KA2), Known Antibody 3 (KA3), or Known Antibody 4 (KA4).

In some specific embodiments, KA1 is an antibody which includes CDR-H1-3 as shown in SEQ ID NO.7~9; and CDR-L1~3 as shown in SEQ ID NO.10~12.

In some specific embodiments, KA2 is an antibody which includes CDR-H1~3 as shown in SEQ ID NO.13~15; and CDR-L1~3 as shown in SEQ ID NO.16~18.

In some specific embodiments, KA3 is an antibody which includes CDR-H1~3 as shown in SEQ ID NO.19~21; and CDR-L1~3 as shown in SEQ ID NO.22~24.

In some specific embodiments, KA4 is an antibody which includes CDR-H1~3 as shown in SEQ ID NO.25~27; and CDR-L1~3 as shown in SEQ ID NO.28~30.

The capture antibody and the detection antibody can be exchanged with each other, that is, one antibody can be used as the detection antibody, and also can be uses as the capture antibody.

Preferably, the antibody pair includes a capture antibody and a detection antibody, and the capture antibody is an antibody which includes CDR-H1 as shown in SEQ ID NO.1 and CDR-H2 as shown in SEQ ID NO.2, and CDR-H3 as shown in SEQ ID NO.3; and CDR-L1 as shown in SEQ ID NO.4, CDR-L2 as shown in SEQ ID NO.5, and CDR-L3 as shown in SEQ ID NO.6; the detection antibody is KA4.

In yet another aspect, the present disclosure provides a kit, comprising the antibody or antigen-binding fragment(s) thereof, or the conjugate thereof.

Preferably, the kit further includes a second antibody, which specifically recognizes the antibody or its antigen-binding fragment(s); optionally, the second antibody further includes a detectable label, such as radioisotopes, fluorescent substances, luminescence substances, coloured substances or enzymes.

The present disclosure provides a kit comprising the antibody pair of the present disclosure; optionally, the detection antibody includes a detectable label, such as a radioisotope, a fluorescent substance, a luminescent substance, a colored substance or an enzyme.

In yet another aspect, the present disclosure provides the use of the antibody or antigen-binding fragment(s) thereof in any one of the present disclosure or the antibody pair of the present disclosure or the conjugate of the present disclosure in the preparation of a kit, which is used to detect the presence or level of cardiac troponin I in a sample from a subject.

In a specific embodiment, the present disclosure provides the use of the antibody or antigen-binding fragment(s) thereof of any one of the present disclosure or the antibody pair of the present disclosure or the conjugate of the present disclosure in the preparation of a kit for assisting diagnosis of myocardial injury.

In some specific embodiments, the myocardial injury is caused by myocardial infarction, coronary sclerosis syndrome, myocarditis, pericarditis, and the like.

In a specific embodiment, the present disclosure provides the use of the antibody or antigen-binding fragment(s) thereof of any one of the present disclosure or the antibody pair of the present disclosure or the conjugate of the present disclosure in the preparation of a kit for assisting diagnosis of myocardial infarction.

In yet another aspect, the present disclosure provides a method for producing the antibody or antigen-binding fragment(s) thereof of the present disclosure, comprising culturing the host cell of the present disclosure under suitable conditions, and recovering the antibody or antigen-binding fragment(s) thereof from the cell culture.

In a specific embodiment, the present disclosure provides the antibody or antigen-binding fragment(s) thereof, comprising the isolated antibody or antigen-binding fragment(s) thereof specifically binds to cardiac troponin I secreted by a hybridoma cell strain deposited at the National Bioresource Center, Russian National Collection of Industrial Microorganisms (VKPM) of the National Research Center "Kurchatov Institute," at the address of Dorozhnyi Proezd, 1, Moscow, 117545 Russia.

In yet another aspect, the present disclosure provides a method for assisting diagnosis of myocardial injury, comprising the step of using the antibody or antigen-binding fragment(s) thereof of the present disclosure to a sample from a subject.

The preservation of the present invention is as follows:

The hybridoma cell strain capable of secreting new antibody 1 (NA1), with an accession/deposit number of H-202, was deposited at the National Bioresource Center, Russian National Collection of Industrial Microorganisms (VKPM) of the National Research Center "Kurchatov Institute" on Sep. 13, 2023 and accepted on Sep. 24, 2023.

BRIEF DESCRIPTION OF THE DRAWINGS

FIG. 1 shows the result of the prognostic performance of the antibody pair of the present disclosure to patient A with acute myocardial injury.

DETAILED DESCRIPTION

In the present disclosure, unless otherwise indicated, the scientific and technical terms used in this disclosure shall have the meaning commonly understood by a person skilled in the art. In addition, the cell culture, molecular genetics, nucleic acid chemistry, and immunology related laboratory procedures used in this disclosure are the general procedures used in the relevant fields. Meanwhile, in order to better understand the disclosure, the definitions and interpretations of relevant terms are provided below.

Unless otherwise indicated, the term "isolated molecule" (where the molecule is, for example, a polypeptide, a polynucleotide, or an antibody or fragment thereof) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody or antigen-binding fragment thereof of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody (or simply "antibody portion"), as used interchangeably herein, refers to one or more fragments of an antibody that retain the ability to specifically bind to an antigen (e.g., cardiac troponin). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain FAT (scFv)). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

Antibodies may be derived from any mammal, including, but not limited to, humans, monkeys, pigs, horses, rabbits, dogs, cats, mice, etc., or other animals such as birds (e.g. chickens), fish (e.g., sharks) and camelids (e.g., llamas).

A "variable region" of an antibody refers to the variable region of the antibody light chain (VL) or the variable region of the antibody heavy chain (VH), either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region.

A variant antibody may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid.

As outlined elsewhere herein, certain positions of the antibody molecule can be altered. By "position" as used herein is meant a location in the sequence of a protein. Positions may be numbered sequentially, or according to an established format, for example the EU index and Kabat index can be used to number amino acid residues of an antibody. Corresponding positions are determined as outlined above, generally through alignment with other parent sequences.

Generally, the term "epitope" refers to the area or region of an antigen to which an antibody specifically binds, e.g., an area or region comprising a contact residue that interacts with the antibody. Thus, the term "epitope" refers to that portion of a molecule capable of being recognized by and bound by an antibody at one or more of the antibody's antigen-binding regions. Typically, an epitope is defined in the context of a molecular interaction between an antibody, or antigen-binding fragment thereof, and its corresponding antigen. Epitopes often consist of a surface grouping of molecules such as amino acids or sugar side chains and have specific three-dimensional structural characteristics as well as specific charge characteristics.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

The term "dissociation constant" is sometimes used interchangeably with "equilibrium dissociation constant", and refers to the value obtained in a titration measurement at equilibrium, or by dividing the dissociation rate constant (Koff) by the association rate constant (Kon). The association rate constant, the dissociation rate constant and the equilibrium dissociation constant are used to represent the binding affinity of an antibody to an antigen. Methods for determining association and dissociation rate constants are well known in the art.

Binding affinity between two molecules, e.g. an antibody, or fragment thereof, and an antigen, through a monovalent interaction may be quantified by determination of the dissociation constant (KD). In turn, KD can be determined by measurement of the kinetics of complex formation and dissociation using, e.g., the surface plasmon resonance (SPR) method (Biacore). The rate constants corresponding to the association and the dissociation of a monovalent complex are referred to as the association rate constants Ka (or Kon) and dissociation rate constant Kd (or Koff), respectively. KD is related to Ka and Kd through the equation KD=Kd/Ka. The value of the dissociation constant can be determined directly by well-known methods, and can be computed even for complex mixtures by methods such as those, for example, set forth in Caceci et al. (1984, Byte 9: 340-362).

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats.

Hereinafter, the present disclosure will be described in detail with reference to specific embodiments and examples, and the advantages and various effects of the present disclosure will be more clearly presented therefrom. Those skilled in the art should understand that these specific embodiments and examples are used to illustrate the present disclosure, rather than limit the present disclosure.

Example 1. Screening of Anti-Cardiac Troponin I Antibodies

Recombinant soluble cardiac troponin I was expressed in *E. coli* and further purified. The resulting purified protein solution was concentrated, stored below –80° C., and the purity was confirmed by SDS-PAGE and molecular sieve chromatography (SEC).

Recombinant soluble cardiac troponin I was used to immunize mice. The immunized hybridoma cells were screened to obtain hybridoma cells that produced anti-cardiac troponin I. RNA was extracted from the screened hybridoma cells and their antibody-producing sequences were sequenced. Partial sequencing results are shown in Table 1 (amino acid sequence) below.

TABLE 1

| Antibody name | CDR1 | CDR2 | CDR3 |
|---|---|---|---|
| | | Heavy chain | |
| NA1 | NYAMS | TISSGSSHTFYSDSVKG | ARRWDGAIDY |
| | | Light chain | |
| NA1 | RASQDISNYLN | YTSRLHS | QQGHTLPLT |

Example 2. Production of Anti-Cardiac Troponin I Antibodies

Monoclonal antibody new antibody 1 (NA1) were raised in mouse ascitic fluid after intraperitoneal injection of 5 selected hybridoma clones.

Antibodies were purified from ascitic fluid (NA1) by using Protein A affinity chromatography. The resin was from GE Healthcare Life Sciences (Piscataway, NJ), and purification was carried out according to manufacturer's instructions. Purified monoclonal antibodies were stored as suspensions in 50% ammonium sulfate at 4° C.

Example 3. Measurement of the Affinity of Antibodies

The antibody prepared in Example 2 was dissolved in PBS (5 pg/mL), and was applied to the sensor, and the sensor was blocked. Antigen (cardiac troponin complex) was then administered at concentrations of 10, 30 and 90 nM, respectively. Finally, the affinity of the antibody was measured according to biofilm interference, and the measurement results are shown in Table 2. It can be seen from Table 2 that the antibodies of the present disclosure all have good affinity for the target cardiac troponin.

TABLE 2

| Antibody | Ka(1/Ms) | Kd(1/s) | KD(M) |
| --- | --- | --- | --- |
| NA1 | 4.38E+04 | 5.29E−04 | 1.21E−08 |

Example 4. Testing of Epitope Specificity of Antibodies

Epitope specificity of monoclonal antibodies was determined by ELISA with short (15-20 a.a.r.) peptides, containing amino-acid sequences from 18 to 200 a.a.r. (manufacturer: Peptides 2.0). Peptides were conjugated with BSA by using sulfo-SMCC obtained from Pierce (Rockford, IL) according to manufacturer's instructions. BSA was linked to peptides by one additional cysteine residue from the N-terminus. For the conjugation 2.5 mg of carrier protein—bovine serum albumin (BSA) (obtained from Sigma Chemicals, St. Louise, Mo.) was dissolved in PBS to the concentration 10 mg/ml. Two milligrams of sulfo-SMCC, dissolved in 0.1 ml dimethyl sulfoxide, were added to the protein solution. Reaction of carrier protein activation was carried out for 2 hours at room temperature. Excess of sulfo-SMCC was removed by gel-filtration using NAP-5 columns (obtained from GE Healthcare Life Sciences, Piscataway, NJ). NAP-5 columns were pre-equilibrated with 10 mM KH2PO4, 150 mM NaCl, pH 7.2. Then 2 mg of synthetic peptide-1 or peptide-2 were added to protein solution to start the conjugation. This reaction was carried out for 2 hours on ice with constant shaking. Unreacted peptide fraction was removed from protein-peptide conjugate by using gel-filtration NAP-5 columns, pre-equilibrated with PBS. The conjugation of the peptides to appropriate carrier protein was confirmed by 3-5 kDa increase in the protein molecular weight revealed by using sodium dodecyl sulphate poly-acrylamide gel electrophoresis. Conjugates were aliquoted and stored at −20° C. until use.

The BSA-synthetic peptide was diluted to a 5 μg/mL solution with 0.1 M NaHCO3 (pH 9.6) and added to a highly adsorbed 96-well plate at 100 μL per well. Incubate overnight at 4° C. The solution in the plate was dried, and 400 μL of PBS solution containing 1% BSA was added to each well, and stand for 3 hours at room temperature for blocking. The solution was dried and the well of plate was washed three times with PBS containing 0.05% Tween-20. The 12 antibodies were diluted to 100 pg/mL in PBS containing 1% BSA, 100 pL was added to each well, and incubated at 37° C. for 1.5 hours. The solution was dried and washed 3 times with PBS containing 0.05% Tween-20. Prepare a 1/2000-fold dilution of goat anti-mouse IgG-HRP solution in PBS solution containing 1% BSA, add 100 μuL of the solution to each well, and incubate at 37° C. for 1.5 hours. The solution was dried and washed 3 times with PBS containing 0.05% Tween-20. 100 μL of TMB substrate solution was added to each well, incubated at room temperature for 30 minutes, and terminated with 100 μt of 0.16M sulfuric acid solution. Read the absorbance at OD450 on a microplate reader.

According to the above method, antibodies were detected, and the results were as follows:

Mab NA1 recognized peptides 78-93 amino acid residues (a.a.r) and 83-100, thus the epitope for these MAbs is within 83 and 93 a.a.r.

Example 5. Sandwich Immunoassay Using Antibody Pair

To find the best antibody pair, a sandwich immunoassay was used. The detection ability of human cardiac troponin was detected by combining antibodies that recognize different epitopes. In addition to the antibodies used in the present disclosure, KA1 (known antibody 1), KA2 (known antibody 2), KA3 (known antibody 3) (cat #RC4T21), and KA4 (known antibody 4) (cat #4TC2) antibodies from HyTest were used, and the sequence of those antibodies are shown in Table 3 (amino acid sequence) below.

TABLE 3

| Antibody name | CDR1 | CDR2 | CDR3 |
| --- | --- | --- | --- |
| | | Heavy chain | |
| KA1 | GIDLGSFA | INSAGIL | ARLYDL |
| KA2 | GIDLAGYA | IASDGEK | ARFYDL |
| KA3 | GIDLGSFA | INSEDIL | ARFWDL |
| KA4 | GYTFTLYV | INPYIDGT | ARSGYGNYGLAWLAY |
| | | Light chain | |
| KA1 | QSVYDNNA | DASKLAS | LGDYDCSSADCYA |
| KA2 | ESVYDNNA | DASKVAS | LGDYDCDSGDCYV |
| KA3 | QSVYDGTA | DASKLAS | LGDYDCSSGDCYV |
| KA4 | TGAVTTSNY | GSNNRAP | GLLYSNNWV |

The detection ability of antibody pairs was determined using dissociation-enhanced lanthanide fluorescent immunoassays and chemiluminescence immunoassays.

To perform sandwich fluorescent immunoassays, detection MAbs labeled with stable Eu3+ chelate were used as described by Hyytiä et al., 2010. Capture antibodies in this assay were unlabeled. Capture antibodies 100 pL per well (2 μg/ml) in PBS, were incubated in 96-well immunoassay plates for 30 min at room temperature upon constant shaking. The plates were washed with 10 mM Tris-HC1 (pH 7.8)

buffer, supplemented by 0.15 M NaCl, 0.025% Tween 20 and 0.5 g/L NaN3 (Washing Solution, WS). After washing 0.05 ml of buffer B (50 mM Tris-HC1 buffer, pH 7.8, 0.9% NaCl, 0.01% Tween 40, 0.5% BSA and 0.05% NaN3), the solution (2 mg/L) of detection antibodies were added to the plates. Immediately after detection MAbs 25 µL Ag (native human cardiac troponin complex) standard solutions in 50 mM Tris-HC1 buffer, pH 7.8, 150 mM KC1, 5 mM $CaCl_2$, 7.5% BSA and 0.15% were added. The plates were incubated for 30 min at room temperature with constant shaking. After washing with WS, 0.1 ml of DELFIA® Enhancement solution (Perkin Elmer, Finland) per well were added and incubated for 10 min at room temperature with gentle shaking. Fluorescence of $Eu^{3+}$ was measured on a Victor 1420 multilabel counter (Wallac-Perkin Elmer, Finland). The fluorescence was expressed in counts per second (CPS).

To perform sandwich chemiluminescent immunoassays (CLIA), detection MAbs were labeled with biotin derivative. Capture antibodies (unlabeled), 100 µL per well (2 µg/ml) in phosphate buffer saline (PBS), were incubated in 96-well immunoassay plates for 30 min at room temperature upon constant shaking. The plates were washed with PBS supplemented by 0.025 Tween 20 and 0.05% ProClin (PBST). After washing 0.05 ml of the buffer B, the solution (2 mg/L) of detection antibodies in CLIA assay buffer (PBST, containing 75 g/L BSA) were added to the plates. Immediately after detection MAbs 25 µL Ag (native hc troponin complex) standard solutions in 50 mM Tris-HC1 buffer, pH 7.8, 150 mM KC1, 5 mM $CaCl_{22}$, 7.5% BSA and 0.15% $NaN_3$ were added. The plates were incubated for 30 min at room temperature with constant shaking. After washing with PBST, 0.1 ml of Pierce™ Streptavidin Poly-HRP per well (5 ng/ml in CLIA assay buffer) were added and incubated for 5 min at room temperature with gentle shaking. After washing with PBST (6 times) the SuperSignal™ ELISA Femto Substrate was added. Incubation time was 1 min, RT and gentle shaking. Chemiluminescence was measured on a EnVision 2105 multimode plate reader (Perkin Elmer, Finland). The chemiluminescence was expressed in counts per second (CPS).

Sandwich immunoassays were able to detect only hcTnl and had no cross-reaction (or less than 0.03%) with skeletal isoforms of TnI.

Limit of Blank (LOB) and LOD determination were performed according to Clinical and Laboratory Standard Institute (CLSI) recommendations. The measurement results are shown in Tables 4 and 5.

It shows that the sensitivity of these antibody pairs is below 10 pg/ml, which can meet the performance requirements for the development of high-sensitivity troponin kits.

TABLE 4

| LOD of Antibody Pairs in DELFIA | | |
| --- | --- | --- |
| Capture antibody | Dection antibody | LOD, pg/ml |
| NA1 | KA4 | 1.0 |

TABLE 5

| LOD of Antibody Pairs in CLIA | | |
| --- | --- | --- |
| Capture antibody | Dection antibody | LOD, pg/ml |
| KA2 | NA1 | 1.0 |

Example 6. Prognosis Performance of Acute Myocardial Injury Patients by Hs-cTnI Specific Immunoassay To determine the prognostic performance of the hs-cTnI sandwich immunoassay, serum or plasma samples from different acute myocardial infarction patients at different time points were dynamically monitored. The results showed that hs-cTnI values were highly consistent with disease stage progression. Details are as follows:

Patient A: 71 yr female, sent to ED due to chest pain, diagnosed as STEAMI, at this point, the first test is carried out using antibody pair NA1/KA4 (test 1); received percutaneous coronary intervention immediately, coronary stents and revascularization. Then breath circulation was stable, and transferred to cardiology department for general treatment, at this point, the second test was performed (test 2), and the value of cardiac troponin decreased significantly compared with the first test. During treating process, the 3rd to 8th tests were carried out (test 3-8), and the value of cardiac troponin continued to decrease, as shown in FIG. 2. These tests are carried out by NA1/KA4 pair assay.

Example 7. Measurement of the Specificity of Antibodies

In order to evaluate the potential cross-reactivity of antibodies, the following substances were added at the concentration (1000 ng/m1) indicated to a sample with known cTnI concentration (0.7 ng/L). Results from the spiked samples were compared with those of unspiked control samples. All antibodies show high specificity for cTnI. Percent cross-reactivity is calculated as:

$$\% \text{ cross-reactivity} = \frac{(\text{concentration of spiked sample} - \text{concentration of unspiked sample})}{\text{concentration of substance}} \times 100$$

TABLE 6

| Substance | Concentration (ng/mL) | NA1 % cross-reactivity |
| --- | --- | --- |
| Skeletal troponin I | 1000 | ND[a] |
| Skeletal troponin T | 1000 | ND[a] |
| Cardiac troponin T | 1000 | 1.00E–04 |
| Troponin C | 1000 | 1.00E–04 |
| Actin | 1000 | ND[a] |
| Tropomyosin | 1000 | 1.70E–04 |
| Myosin light chain | 1000 | ND[a] |
| Myoglobin | 1000 | ND[a] |
| CK-MB | 1000 | ND[a] |

ND[a] = Not Detectable

SEQUENCE LISTING

Sequence total quantity: 30
SEQ ID NO: 1              moltype = AA   length = 5
FEATURE                   Location/Qualifiers
source                    1..5
                          mol_type = protein
                          organism = synthetic construct
SEQUENCE: 1
NYAMS                                                             5

SEQ ID NO: 2              moltype = AA   length = 17
FEATURE                   Location/Qualifiers
source                    1..17
                          mol_type = protein
                          organism = synthetic construct
SEQUENCE: 2
TISSGSSHTF YSDSVKG                                                17

SEQ ID NO: 3              moltype = AA   length = 10
FEATURE                   Location/Qualifiers
source                    1..10
                          mol_type = protein
                          organism = synthetic construct
SEQUENCE: 3
ARRWDGAIDY                                                        10

SEQ ID NO: 4              moltype = AA   length = 11
FEATURE                   Location/Qualifiers
source                    1..11
                          mol_type = protein
                          organism = synthetic construct
SEQUENCE: 4
RASQDISNYL N                                                      11

SEQ ID NO: 5              moltype = AA   length = 7
FEATURE                   Location/Qualifiers
source                    1..7
                          mol_type = protein
                          organism = synthetic construct
SEQUENCE: 5
YTSRLHS                                                           7

SEQ ID NO: 6              moltype = AA   length = 9
FEATURE                   Location/Qualifiers
source                    1..9
                          mol_type = protein
                          organism = synthetic construct
SEQUENCE: 6
QQGHTLPLT                                                         9

SEQ ID NO: 7              moltype = AA   length = 8
FEATURE                   Location/Qualifiers
source                    1..8
                          mol_type = protein
                          organism = synthetic construct
SEQUENCE: 7
GIDLGSFA                                                          8

SEQ ID NO: 8              moltype = AA   length = 7
FEATURE                   Location/Qualifiers
source                    1..7
                          mol_type = protein
                          organism = synthetic construct
SEQUENCE: 8
INSAGIL                                                           7

SEQ ID NO: 9              moltype = AA   length = 6
FEATURE                   Location/Qualifiers
source                    1..6
                          mol_type = protein
                          organism = synthetic construct
SEQUENCE: 9
ARLYDL                                                            6

SEQ ID NO: 10             moltype = AA   length = 8
FEATURE                   Location/Qualifiers
source                    1..8
                          mol_type = protein
                          organism = synthetic construct

```
SEQUENCE: 10
QSVYDNNA                                                                    8

SEQ ID NO: 11        moltype = AA   length = 7
FEATURE              Location/Qualifiers
source               1..7
                     mol_type = protein
                     organism = synthetic construct
SEQUENCE: 11
DASKLAS                                                                     7

SEQ ID NO: 12        moltype = AA   length = 13
FEATURE              Location/Qualifiers
source               1..13
                     mol_type = protein
                     organism = synthetic construct
SEQUENCE: 12
LGDYDCSSAD CYA                                                             13

SEQ ID NO: 13        moltype = AA   length = 8
FEATURE              Location/Qualifiers
source               1..8
                     mol_type = protein
                     organism = synthetic construct
SEQUENCE: 13
GIDLAGYA                                                                    8

SEQ ID NO: 14        moltype = AA   length = 7
FEATURE              Location/Qualifiers
source               1..7
                     mol_type = protein
                     organism = synthetic construct
SEQUENCE: 14
IASDGEK                                                                     7

SEQ ID NO: 15        moltype = AA   length = 6
FEATURE              Location/Qualifiers
source               1..6
                     mol_type = protein
                     organism = synthetic construct
SEQUENCE: 15
ARFYDL                                                                      6

SEQ ID NO: 16        moltype = AA   length = 8
FEATURE              Location/Qualifiers
source               1..8
                     mol_type = protein
                     organism = synthetic construct
SEQUENCE: 16
ESVYDNNA                                                                    8

SEQ ID NO: 17        moltype = AA   length = 7
FEATURE              Location/Qualifiers
source               1..7
                     mol_type = protein
                     organism = synthetic construct
SEQUENCE: 17
DASKVAS                                                                     7

SEQ ID NO: 18        moltype = AA   length = 13
FEATURE              Location/Qualifiers
source               1..13
                     mol_type = protein
                     organism = synthetic construct
SEQUENCE: 18
LGDYDCDSGD CYV                                                             13

SEQ ID NO: 19        moltype = AA   length = 8
FEATURE              Location/Qualifiers
source               1..8
                     mol_type = protein
                     organism = synthetic construct
SEQUENCE: 19
GIDLGSFA                                                                    8

SEQ ID NO: 20        moltype = AA   length = 7
FEATURE              Location/Qualifiers
source               1..7
                     mol_type = protein
```

-continued

```
                        organism = synthetic construct
SEQUENCE: 20
INSEDIL                                                                          7

SEQ ID NO: 21           moltype = AA   length = 6
FEATURE                 Location/Qualifiers
source                  1..6
                        mol_type = protein
                        organism = synthetic construct
SEQUENCE: 21
ARFWDL                                                                           6

SEQ ID NO: 22           moltype = AA   length = 8
FEATURE                 Location/Qualifiers
source                  1..8
                        mol_type = protein
                        organism = synthetic construct
SEQUENCE: 22
QSVYDGTA                                                                         8

SEQ ID NO: 23           moltype = AA   length = 7
FEATURE                 Location/Qualifiers
source                  1..7
                        mol_type = protein
                        organism = synthetic construct
SEQUENCE: 23
DASKLAS                                                                          7

SEQ ID NO: 24           moltype = AA   length = 13
FEATURE                 Location/Qualifiers
source                  1..13
                        mol_type = protein
                        organism = synthetic construct
SEQUENCE: 24
LGDYDCSSGD CYV                                                                   13

SEQ ID NO: 25           moltype = AA   length = 8
FEATURE                 Location/Qualifiers
source                  1..8
                        mol_type = protein
                        organism = synthetic construct
SEQUENCE: 25
GYTFTLYV                                                                         8

SEQ ID NO: 26           moltype = AA   length = 8
FEATURE                 Location/Qualifiers
source                  1..8
                        mol_type = protein
                        organism = synthetic construct
SEQUENCE: 26
INPYIDGT                                                                         8

SEQ ID NO: 27           moltype = AA   length = 15
FEATURE                 Location/Qualifiers
source                  1..15
                        mol_type = protein
                        organism = synthetic construct
SEQUENCE: 27
ARSGYGNYGL AWLAY                                                                 15

SEQ ID NO: 28           moltype = AA   length = 9
FEATURE                 Location/Qualifiers
source                  1..9
                        mol_type = protein
                        organism = synthetic construct
SEQUENCE: 28
TGAVTTSNY                                                                        9

SEQ ID NO: 29           moltype = AA   length = 7
FEATURE                 Location/Qualifiers
source                  1..7
                        mol_type = protein
                        organism = synthetic construct
SEQUENCE: 29
GSNNRAP                                                                          7

SEQ ID NO: 30           moltype = AA   length = 9
FEATURE                 Location/Qualifiers
source                  1..9
```

-continued

```
                          mol_type = protein
                          organism = synthetic construct
SEQUENCE: 30
GLLYSNNWV                                                                    9
```

What is claimed is:

1. An isolated antibody or antigen-binding fragment(s) thereof that specifically binds to cardiac troponin I, having a heavy chain and a light chain, wherein the heavy chain comprises a heavy chain variable region, and the light chain comprises a light chain variable region, wherein the heavy chain variable region comprises:
- a. CDR-H1, having the amino acid sequence of SEQ ID NO.1;
- b. CDR-H2, having the amino acid sequence of SEQ ID NO.2; and
- c. CDR-H3, having the amino acid sequence of SEQ ID NO.3, wherein the light chain variable region comprises:
- a. CDR-L1, having the amino acid sequence of SEQ ID NO.4;
- b. CDR-L2, having the amino acid sequence of SEQ ID NO.5; and
- c. CDR-L3, having the amino acid sequence of SEQ ID NO.6.

2. The isolated antibody or antigen-binding fragment(s) thereof according to claim 1, wherein, the antibody or antigen-binding fragment(s) thereof has a KD value of less than 20 nM.

3. The isolated antibody or antigen-binding fragment(s) thereof according to claim 2, wherein, the antibody or antigen-binding fragment(s) thereof has a KD value of less than 5 nM.

4. The isolated antibody or antigen-binding fragment(s) thereof according to claim 3, wherein, the antibody or antigen-binding fragment(s) thereof has a KD value of less than 2 nM.

5. A conjugate, comprising the antibody or antigen-binding fragment(s) thereof according to claim 1 and a coupling moiety, wherein the coupling moiety is a detectable marker.

6. An antibody pair, comprising a capture antibody and a detection antibody, wherein the capture antibody and the detection antibody target different epitopes of cardiac troponin I, wherein one of the capture antibody and the detection antibody is selected from an antibody or antigen-binding fragment(s) thereof according to claim 1, and the other is selected from a group consisting of Known Antibody 1, Known Antibody 2, Known Antibody 3, or Known Antibody 4 antibody, wherein, the Known Antibody 1 is an antibody which comprises CDR-H1-3 having respective amino acid sequence of SEQ ID NO: 7-9; and CDR-L1-3 having respective amino acid sequence of SEQ ID NO: 10-12;

the Known Antibody 2 is an antibody which comprises CDR-H1-3 having respective amino acid sequence of SEQ ID NO: 13-15; and CDR-L1-3 having respective amino acid sequence of SEQ ID NO: 16-18;

the Known Antibody 3 is an antibody which comprises CDR-H1-3 having respective amino acid sequence of SEQ ID NO: 19-21; and CDR-L1-3 having respective amino acid sequence of SEQ ID NO: 22-24;

the Known Antibody 4 is an antibody which comprises CDR-H1-3 having respective amino acid sequence of SEQ ID NO: 25-27; and CDR-L1-3 having respective amino acid sequence of SEQ ID NO: 28-30.

7. The antibody pair according to claim 6, wherein, the capture antibody is an antibody which comprises CDR-H1 having the amino acid sequence of SEQ ID NO.1 and CDR-H2 having the amino acid sequence of SEQ ID NO.2, and CDR-H3 having the amino acid sequence of SEQ ID NO.3; and CDR-L1 having the amino acid sequence of SEQ ID NO.4, CDR-L2 having the amino acid sequence of SEQ ID NO.5, and CDR-L3 having the amino acid sequence of SEQ ID NO.6; the detection antibody is the Known Antibody 4.

8. A kit, comprising the antibody or antigen-binding fragment(s) thereof according to claim 1.

9. The kit according to claim 8, wherein the kit further comprises a second antibody, which specifically recognizes the antibody or antigen-binding fragment(s) thereof.

10. A kit, comprising the antibody pair of claim 6.

11. A method of detecting the presence or a level of cardiac troponin I in a sample from a subject comprising contacting the sample with the antibody or antigen-binding fragment(s) thereof according to claim 1.

12. A method for assisting diagnosis of myocardial injury comprising detecting the presence or a level of cardiac troponin I in a sample from a subject by contacting the sample with the antibody or antigen-binding fragment(s) thereof according to claim 1.

13. An isolated antibody or antigen-binding fragment(s) thereof, wherein, the isolated antibody or antigen-binding fragment(s) thereof specifically binds to cardiac troponin I secreted by a hybridoma cell strain deposited with the Russian National Collection of Industrial Microorganisms (VKPM) with an accession/deposit number of H-202.

* * * * *